United States Patent [19]

Fleet et al.

[11] Patent Number: 5,210,089
[45] Date of Patent: May 11, 1993

[54] D-RHAMNONO-1,5-LACTONE

[75] Inventors: George W. J. Fleet, Oxford; Bryan G. Winchester, London, both of United Kingdom

[73] Assignee: Monsanto Company, St. Louis, Mo.

[21] Appl. No.: 830,826

[22] Filed: Feb. 4, 1992

[51] Int. Cl.$^5$ ..................... C07D 211/42; A01N 43/40
[52] U.S. Cl. .................................. 514/315; 546/242; 549/214
[58] Field of Search ........................ 546/242; 514/315; 549/214

[56] References Cited

U.S. PATENT DOCUMENTS

| 5,011,929 | 4/1991 | Fleet et al. | 546/242 |
| 5,013,842 | 5/1991 | Fleet et al. | 546/242 |
| 5,017,704 | 5/1991 | Fleet et al. | 546/242 |

Primary Examiner—C. Warren Ivy
Assistant Examiner—Raymond Covington
Attorney, Agent, or Firm—Scott J. Meyer

[57] ABSTRACT

The novel D-rhamnono-? ,5-lactone and a novel method of synthesis of said compound from the monoacetonide of L-gulono-γ-lactone is disclosed. D-Rhamnono-1,5-lactone is a potent inhibitor of α-and β-mannosidases but not of α-rhamnosidase.

3 Claims, No Drawings

D-RHAMNONO-1,5-LACTONE

BACKGROUND OF THE INVENTION

This invention relates to the novel D-rhamnonoi-1,5-lactone and, more particularly, to the synthesis of D-rhamnono-1,5-lactone from D-gulonolactone.

In general, removal of the anomeric hydroxyl group from a pyranose sugar and replacement of the ring oxygen by a nitrogen atom reliably produces compounds which are effective inhibitors of the corresponding glycosidases [G. Legler, *Adv. Carbohydr. Chem. Biochem.* 48, 319 (1990); G. W. J. Fleet et al., Plagiarizing Plants: Aminosugars as a Class of Glycosidase Inhibitors, In: *Bioactive Comoounds from Plants*, p. 112–125, Wiley, Chichester (Ciba Found. Symp. 154), (1990); A. Straub et al., *J. Org. Chem.* 55, 3926 (1990); C.-H. Wong et al., *Tetrahedron Lett.* 32, 4867 (1991); G. Gradnig et al., Tetrahedron Lett. 32, 4889 (1991); P. S. Liu et al., *Tetrahedron Lett.* 32, 5853 (1991); L. E. Fellows and R. J. Nash, *Sci. Progress* 74. 245 (990)]. For example, deoxymannojirimycin (1), isolated from *Lonchocarpus sericeus*. [L. E Fellows et al., *J. Chem. Soc. Chem. Commun.*, 977 (1979)] is a potent inhibitor of glycoprotein processing mannosidase I [U. Fuhrmann et al., *Nature* 307, 755 (1984); A. D. Elbein et al., *Arch. Biochem. Biophys.* 235, 579 (1984)], and a bovine α-L-fucosidase [S. V. Evans et al., *Phytochemistry* 24, 1953 (1985)]. The corresponding lactam, D-mannonolactam (2), is a powerful inhibitor of human lysosomal and rat epidodymal α-mannosidases, and of apricot β-glucosidase [T. Niwa et al., J. Anibot. 37. 1579 (1984)]. Many mannopyranosidases are also inhibited by nitrogen analogues of mannofuranose. Thus, 1,4-dideoxy-1,4-iminomannitol (3) [G. W. J Fleet et al., *J. Chem. Soc. Chem. Commun.* 1240 (1984); G. W. J. Fleet et al., *Tetrahedron Lett.* 30, 7261 (1989)] is a strong of many mannosidases [Cenci di Bello et al., *Biochem. J. 259, 855* (1989)] including a mannosidase of glycoprotein processing [P. F. Daniel et al., *Glycoconjugate J.* 6, 229 (1989); G. Palmartczky et al., *Arch. Biochem. Biophys.* 242, 35 (1958)]. Also, the 6-deoxyderivative (4) is an excellent inhibitor of human liver [A. J. Fairbanks et al., Tetrahedron 47, 131–138 (1991)] and other mannosidases. [M. J. Eis et al., *Tetrahedron Lett.* 26, 5398 (1985)].

Rhamnose (6-deoxymannose) residues are widely found intracellularly and extracellularly in plant tissues. The most common form found within the cell is as a component of a glycoside such as flavanoids, phenols, sterols, and coumarins; [G. Avigad, Sucrose and other Disaccharides. In "Plant Carbohydrates 1, Encylopedia of Plant Physiology", Vol. 13A, p. 217–347, Eds. F. A. Loewus and W. Tanner; Springer Verlag]; rhamnose is found typically as a disaccharide conjugate either as an α or β rhamnopyranoside. The degradation of these glycosides is accomplished by a stepwise removal of monosaccharides by exoglycosidases. The aglycones are usually physiologically inactive compounds compared to the glycoside. These exoglycosidases would be an ideal system to test the stereospecificity of inhibition by rhamnose analogues, e.g. naringinase. Rhamnose is also found in intracellular polysaccharides of plants either as a component of cell walls or root mucilage; α-L-rhamnose is a major constituent of rhamnogalacturonan I [M. McNeil et al., *Ann. Rev. Biochem.* 53, 625 (1984)] while L-rhamnose is found in the α- and β-linkages in rhamnogalacturonan II [T. T. Stevenson et al., *Carbohydr. Res.*, 182, 207 (1988)]. If specific exorhamnosidases or endorhamnosidases could be assayed using the polymers as substrates, the use of rhamnose analogues to inhibit the enzyme can provide a useful tool for probing the structure of cell walls.

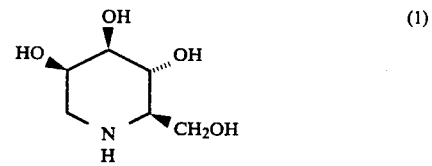
(1)

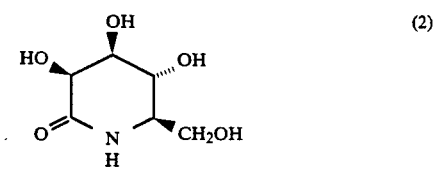
(2)

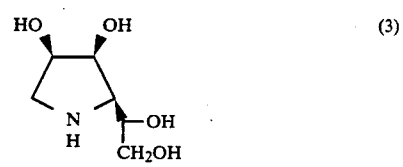
(3)

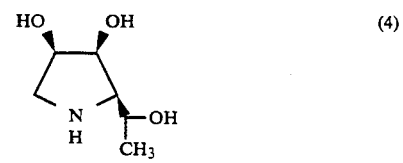
(4)

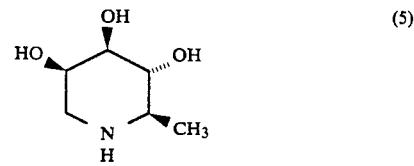
(5)

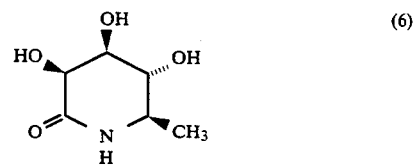
(6)

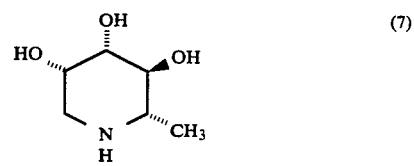
(7)

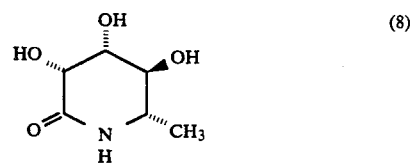
(8)

BRIEF DESCRIPTION OF THE INVENTION

In accordance with the present invention the novel D-rhamnono-1,5-lactone (6) is synthesized from the monoacetonide of D-gulonolactone (9). Surprisingly, the D-rhamnono-1,5-lactone is an inhibitor of α- and β-mannosidases but not of α-rhamnosidase. These unique inhibitory results were unexpected since removal of the anomeric hydroxyl group from a pyranose sugar and replacement of the ring oxygen by a nitrogen atom reliably produces compounds which are effective inhibitors of the corresponding glycosidases (i.e. rhamnosidase), as noted hereinbefore. The inhibition of both α- and β-mannosidases also was unexpected since all the very potent inhibitors of α-mannosidases, such as swainsonine, fail to inhibit β-mannosidase. [Cenci di Bello et al., Biochem. J. 259, 855 (1989).

Even more surprisingly, the D-rhamnono-1,5-lactone is a better inhibitor of α-mannosidase than deoxymannojirimycin (1) which is a well-known potent inhibitor of α-mannosidase. On the other hand, although D-rhamnono-1,5-lactone has the required relative stereochemistry at C2, C3 and C4, it does not show any significant inhibition of α-fucosidase.

Criticality of the D-epimeric configuration of the rhamnono-1,5-lactone for inhibitory activity against α-mannosidase is evident from the test results since the corresponding L-rhamnono-1,5-lactone (8) showed no inhibitory activity against either α-rhamnosidase or β-mannosidase.

The novel D-rhamnono-1,5-lactone of the present invention can be synthesized in a series of steps from the monoacetonide of L-gulono-7-lactone. The L-gulono-γ-lactone is a commercially available product. The acetonide starting material, namely 2,3-O-isopropylidene-L-gulono-γ-lactone (9), also is a known material whose synthesis is described, e.g., in Fleet, U.S. Pat. No. 4,861,892.

A preferred synthesis of the novel D-rhamnono-1,5-lactone comprises the following steps:

(a) 2,3-O-Isopropylidene-L-gulono-7-lactone (9) is converted to the 6-bromo derivative (10) by reaction with carbon tetrabromide and triphenyl phsophine;

(b) The 6-Bromo derivative (10) is subjected to catalytic hydrogenolysis to give the 6-deoxy derivative (11);

(c) The unprotected hydroxyl function in (11) is esterified with triflic anhydride followed by displacement with azide salt to give the azide derivative (12);

(d) The azide derivative (12) is subjected to catalytic hydrogenation to cause reduction to the corresponding amine with spontaneous cyclization to the protected 6-deoxy mannono-lactone (13);

(e) The 6-deoxy-mannono-γ-lactone (13) is deprotected by hydrolysis of the acetonide to give the desired D-rhamnono-1,5-lactone (6).

Reaction Scheme 1 shows the prefered synthesis of D-rhamnono-1,5-lactone.

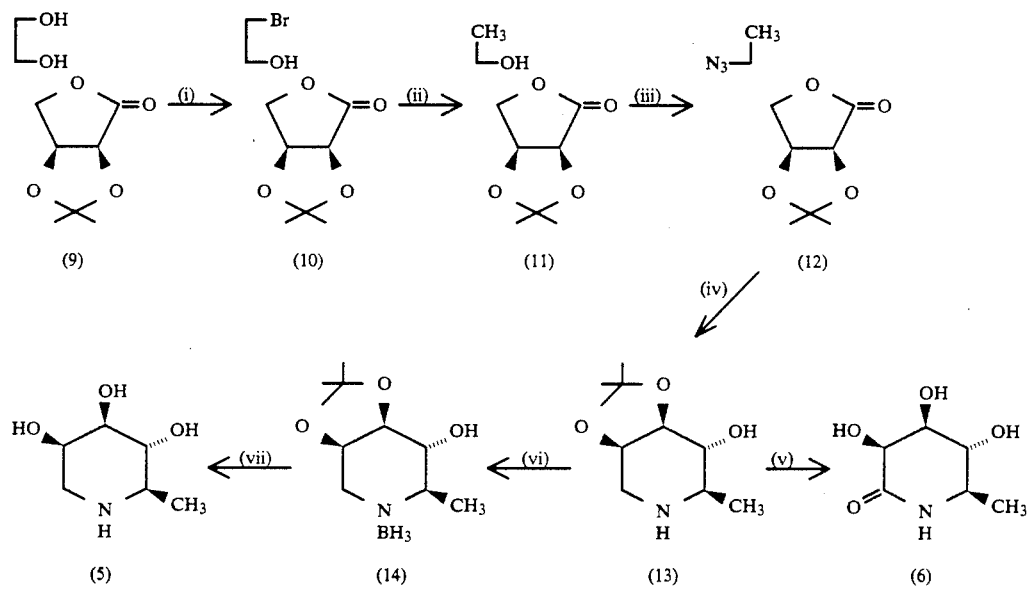

For comparison purposes, the known D-deoxyrhamnojirimycin (5) was also synthesized from the above intermediate lactam (13) as follows: Reduction of lactam (13) with borane:dimethyl sulfide gave the amine borane adduct (14); treatment with hydrochloric acid caused both decomposition of the borane complex and removal of the acetonide which was then converted directed to D-deoxyrhamnojirimycin (5) as the hydrochloride. Also for comparative purposes, the corresponding L-rhamnono-1,5-lactone (8) and L-deoxyrhamnojirimycin (7) were prepared from the monoacetonide of D-gulono-γ-lactone (15) by a similar sequence of steps. The starting monoacetonide of D-gulono-γ-lactone for this synthesis also is a known material as can be seen from Fleet, U.S. Pat. No. 4,861,892. The D- and L-deoxyrhamnojirimycines (5 and 7) have been synthesized previously by a key enzymatic aldol reaction, though no results of inhibition of glycosidases were described. T. Kajimoto et al., J. Am. Chem Soc. 113 6678–6680 (1991).

Reaction Scheme 2 shows the preferred synthesis of L-rhamnono-1,5-lactone.

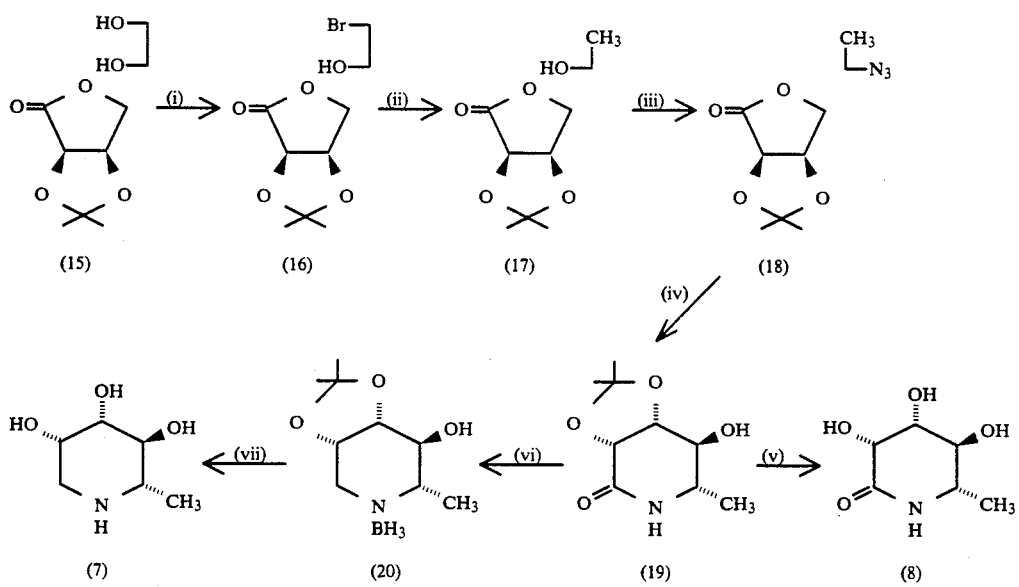

In the foregoing reaction schemes, the reactants are generally used in proportions such as to satisfy the stoichiometry of the reaction steps.

DETAILED DESCRIPTION OF THE INVENTION

In order to further illustrate the invention, the following specific Examples of the laboratory syntheses of the novel D-rhamnono-i,5-lactone and various other compounds as described above were carried out and the final products were assayed for enzyme inhibitory activity. However, it will be appreciated that the invention is not limited to these specific Examples or the details described therein. Thus, it will be appreciated that other conventional hydroxyl protecting agents, e.g. cyclohexylidene, can be used in place of the isopropylidene protecting agent; other conventional organic solvents, e.g. DMF, DMSO and N-methylpyrrolidine, can be used in place of the tetrahydrofuran, pyridine and dichloromethane solvents; other conventional acids can be used in place of the hydrochloric acid; and other azide salts, e.g. potassium, lithium and tetrabutylammonium azides, can be used in place of the sodium azide with substantially equivalent results in the syntheses reactions shown in these examples.

In the enzyme assays, the effects of the test compounds on human liver glycosidases are described and compared with the effects of deoxymannojirimycin (1) mannono-1,5-lactam (2) and 1,4-dideoxy-1,4-iminomannitol (3). The effects on naringinase, a readily available endo-L-rhamnosidase, are also described.

In these Examples, the following general test procedures were used:

General Test Procedures

Melting points were recorded on a Kofler hot block. Proton nuclear magnetic resonance ($\delta$H) spectra were recorded on Varian Gemini 200 (at 200 MHz), Bruker WH 300 (300 MHz), or Bruker AM 500 (500 MHz) spectrometers. Carbon nuclear magnetic resonance ($\delta$C) spectra were recorded on a Varian Gemini 200 (50 MHz) or a Bruker 250 (62.9 MHz) spectrometer. Multiplicities were assigned using DEPT sequence on the Gemini and by off resonance decoupling on the Bruker. Spectra run in $D_2O$ were referenced to methanol as an internal standard. All chemical shifts are quoted on the $\delta$-scale. Infrared spectra were recorded on a Perkin-Elmer 297, or on a Perkin-Elmer 781 spectrophotometer. Mass spectra were recorded on VG Micromass 30F, ZAB 1F, Masslab 20-250 or Trio-1 GCMS (DB-5 column) spectrometers using desorption chemical ionization ($NH_3$DCI), electron impact (EI), chemical ionization ($NH_3$CI) and fast atom bombardment (FAB) techniques, as stated. Optical rotations were measured on a Perkin-Elmer 241 polarimeter with a path length of 1 dm. Concentrations were given in g/100 ml. Hydrogenations were run under an atmosphere of hydrogen gas maintained by inflated balloon. Microanalyses were performed by the microanalysis service of the DysonPerrins laboratory, Oxford UK. Thin layer chromatography (t.l.c.) was carried out on aluminum sheets coated with 60F$_{254}$ silica. Plates were developed using either 5% v/v concentrated sulphuric acid in methanol, 0.2% w/v cerium (IV) sulphate and 5% ammonium molybdate in 2M sulphuric acid and 0.5% ninhydrin in methanol. Flash chromatography was carried out using Sorbsil C60 40/60 silica. Ion-exchange chromatography was performed using Dowex 50W-X8 (H) and Sigma CG 400 (Cl) resins. The resins were washed with 2M hydrochloric acid and 2M sodium hydroxide solution, respectively, and subsequently with distilled water, prior to use. Solvents and commercially available reagents were dried and purified before use according to standard procedures; dichloromethane was refluxed over and distilled from calcium hydride, N,N-dimethylformamide was distilled under reduced pressure from calcium hydride, methanol was distilled from magnesium methoxide, pyridine was distilled from, and stored over, potassium hydroxide and tetrahydrofuran was distilled from a purple solution of sodium benzophenone ketyl immediately before use. Hexane was distilled at 68° C. before use to remove involatile fractions. 2,3-O-Isopropylidene-L-gulono-1,4-lactone (9) [H. Ogura et al., J. Oro. Chem. 37, 72 (1972); G. W. J. Fleet Tetrahedron 45, 319 (1989)]and 2,3-O-isopropylidene-D-gulono-1,4-lactone (15) [L. M. Lerner et al., J. Org. Chem. 33, 1780 (1968)]were prepared from D- and L-Chem. gulonolactones [purchased from the Sigma Chemical Company] as reported previously. See, e.g., Fleet, U.S. Pat. No. 4,861,892. Human liver glycosidases were assayed in the absence and presence [1 mM] of each of the compounds using the appropriate buffered 4-methylumbellifeeryl-glycosides as substrates, as described previously. [B. Winchest et al., Biochem. J. 265, 277 (1990)]. Naringinase was assayed using pnitrophenyl α-L-rhamnoside (1.75 mM) as substrates, according to Romero [C. Romero et al., Anal. Biochem. 149, 566 (1985)].

EXAMPLE 1

6-Bromo-6-deoxy-2,3-O-isopropylidene-L-gulono-γ-lactone (10)

2,3-O-Isopropylidene-L-gulono-γ-lactone (9) (10.0 g, 45.9 mmol) was dissolved in tetrahydrofuran (50 ml) and cooled to 0° C. under nitrogen with stirring. Carbon tetrabromide (14.8 g, 44.7 mmol) and triphenyl phosphine (5.26 g, 58.2 mmol) were added and the reaction allowed to warm to room temperature over 2 h and then stirred at room temperature for 10 h when t.l.c. (ethyl acetate) revealed no starting material ($R_f$ 0.4) and one product ($R_f$ 0.9). The reaction was diluted With ether (150 ml), filtered and the solvent removed under reduced pressure. The residue was purified by flash column chromatography (ether/hexane 2:1), followed by recrystallisation from ether/hexane, to yield 6-bromo-6-deoxy-2,3-O-isopropylidene-L-gulono-7-lactone (9.37 g, 72%), m.p. 86°–87° C. (Found: C, 38.36; H, 4.49%. $C_9H_{13}O_5Br$ requires C, 38.46; H, 4.66%). $[\alpha_{D20}]+52.9$ (c, 1.25 in CHCl$_3$). V$_{max}$ (KBr disc): 3300 cm$^{-1}$ (br, OH), 1790 cm$^{-1}$ (C=O). m/z (CI NH$_3$) 300 and 298 (M+NH$_{4+}$, 100%). $\delta_H$ (CDCl$_3$): 4.90 (1H, s), 4.66 (1H, dd), 4.24 (1H, m), 3.68 (1H,d), 1.50, 1.42 (2×3H, 2 x s, C(CH$_3$)$_2$), 1.44 (2H, m). $\delta_c$ (CDCl$_3$): 173.0 (s, C-1), 114.8 (s, C(CH$_3$)$_2$), 80.2, 76.4, 75.9, 69.5 (4×d, C-2, C-3, C-4, C=5), 33.6 (t, C-6), 26.7, 25.8 (2×q, C(CH$_3$)$_2$).

EXAMPLE 2

6-Deoxy-2,3-O-isopropylidene-L-gulono-γ-lactone (11)

The bromolactone (10) (8.72 g, 31.0 mmol) Was dissolved in ethanol (50 ml). Triethylamine (5 ml) and palladium on carbon (10%, ~50 mg) were added and the reaction was stirred under an atmosphere of hydrogen for 3 h when t.l.c. (ethyl acetate) showed no starting material (R$_1$ 9.9) and one product ($R_f$ 0.7). The reaction mixture was filtered through Celite and the solvent removed under reduced pressure. The residue was recrystallized from ethyl acetate to yield 6-deoxy-2,3-O-isopropylidene-L-gulono-γ-lactone (11) as a white solid, (5.39 g, 86%), m.p. 142°–144° C. (Found: C, 53.59; H, 7.21%. $C_9H_{14}O_5$ requires C, 53.46; H, 6.98%). $[\alpha]_{D20}$ +64.1 (c, 1.2 in EtOH). V$_{max}$ (KBr disc): 3300 cm$^{-1}$ (br, OH), 1790 cm$^{-1}$ (C=O). m/z (CI NH$_3$) 220 (M+NH$_{4+}$, 100%). $\delta_H$ (CD$_3$OD): 4.92 (1H, d), 4.82 (1H, d), 4.27 (1H, dd), 4.04 (1H, m), 1 39, 1.35 (2×3H, 2×s, C(CH$_3$)$_2$), 1.25 (3H, d). $\delta_c$ (CD$_3$OD): 176.4 (s, C-1), 114.4 (s, C(CH$_3$)$_2$), 84.9, 77.6, 77.2, 67.0 (4×d, C-2, C-3, C-4, C-5). 26.5, 25.3 (2×q, C(CH$_3$)$_2$), 17.8 (q, C-6).

EXAMPLE 3

5-Azido-5,6-dideoxy-2,3-O-isopropylidene-D-mannono-δ-lactone (12)

The 6-deoxylactone (11) (5.39 g, 26.7 mmol) was dissolved in a mixture of dichloromethane (75 ml) and pyridine (20 ml) and cooled under dry nitrogen to −20° C. Trifluoromethanesulphonic anhydride (4.95 ml, 29.4 mmol) was added and the reaction stirred for h when t.l.c. (ethyl acetate/hexane 1:1) showed no material ($R_f$ 0.2) and one product ($R_f$ 0.8). The reaction mixture was washed sequentially with 50 ml aliquots of 2M hydrochloric acid, water and brine, dried (magnesium sulphate) and the solvents removed under reduced pressure. The resulting crude triflate was dissolved in dimethylformamide (50 ml) and stirred at room temperature with sodium azide (5.2 g, 80.1 mmol) for 24 h when t.l.c. (ethyl acetate/hexane 1:2) revealed one product ($R_f$ 0.7). Solvents were removed under reduced pressure. The residue was dissolved in ethyl acetate layer was dried (magnesium sulphate) and the solvents removed under reduced pressure. Purification by flash column chromatography (ethyl acetate/hexane 1:3) and recrystallisation from ether gave 5-azizo-5,6-dideoxy, 2,3-O-isopropylidene-D-mannono-7-Iactone (12) as a white solid, (4.0 g, 66%), m.p. 70°–72° C. (Found: C, 47.68; H, 5.64; N, 18.52%. $C_9H_{13}O_4N_3$ requires C, 47.57; H, 5.77; N; 18.49%). $[\alpha]_{D20}+2.64$ (c, 1.1 in CHCl$_3$). V$_{max}$(KBr disc): 2100 cm$^{-1}$ (N$_3$), 1760 cm$^{-1}$ (C=O). m/z (CI NH$_3$): 245 (M+NH$_{4+}$,100%). $\delta_H$ (CDCl$_3$): 4.86 (2H, m), 4.10 (1H, dd), 3.94 (1H, m), 1.46 (3H, d), 1.50, 1.44 (2 x 3H, 2 x s, C(CH$_3$)$_2$) $\delta_c$ (CDCl$_3$): 173.5 (s, C-1), 114.5 (s, C(CH$_3$)$_2$), 80.3, 76.1, 75.7 (3×d, C-2, C3, C$_4$), 55.2 (d, C-5), 26.6, 25.8 (2×q, C(CH$_3$)$_2$), 16.9 (q, C-6).

EXAMPLE 4

6-Deoxy-1,2-O-isopropylidene-D-mannono-δ-Iactam (13)

A solution of the azidolaCtone (12) (4.00 g, 16.8 mmol) in freshly distilled methanol (50 ml) was stirred in the presence of 10% palladium on carbon (~50 mg) under an atmosphere of hydrogen for 5 h when t.l.c. (ethyl t.l.c. (10% methanol in ethyl acetate) showed one major product ($R_f$0.6). The reaction mixture was filtered through Celite and the solvents removed under reduced pressure; the residue was purified by flash column chromatography (l0% ethanol in ethyl acetate) to afford 6-deoxy-1,2-O-isoproylidene-D-mannono-δ-lactam (13), (3.0 g, 89%) as a hydroscopic foam. (Found: C, 53.73; H, 7.86; N, 6.47%. $C_9H_{15}O_4N$ requires C, 53.72; H, 7.51; N, 6.96%). [α]-17.22 (c, 0.76 in CHCl$_3$) V$_{max}$(film) 3300 cm$^{-1}$ (br, OH), 1670 cm$^{-1}$(C=0). m/z (GCMS CI NH$_3$): (202, M+H$^+$, 100%). $\delta_H$ (CDCl)$_3$ 6.58 (1H, s, br), 4.61 (H, d, J 7.9 Hz), 4.29 (1H, d, J 7.7 Hz), 3.38 (2H, m), 1.52, 1.41 (2×3H, 2×s, C(CH$_3$)$_2$), 1.34 (3H, d, J 6.2 H). (CDCl$_3$) 169.7 (s, C-1), 110.7 (s, C(CH$_3$)$_2$), 78.8 72.9 (3×d, C-2, C-3, C-4), 49.5 (d, C-5), 29.8, 24.7 (2×q, C(CH$_3$)$_2$), 17.4 (q, C-6).

EXAMPLE 5

6-Deoxy-D-mannono-δ-lactam [D-Rhamnolactam](6)

The protected mannono-δ-lactam (13) (274 mg, 1.36 mmol) was dissolved in trifluoroacetic acid (4 ml) and water (2 ml) was added. The reaction was left to stand for 2 h when t.l.c. (i% methanol in ethyl acetate) revealed no starting material (R$_1$ 0.6) and one product ($R_f$ 0.1). The solvents were removed under reduced pressure and toluene (2×5 ml) was distilled from the residue. The resulting solid was dissolved in the minimum quantity of hot ethanol and twice the volume of ethyl acetate was added to yield D-rhamnonolactam (6), a white crystalline solid (166 mg, 75%), m.p. 164°–166° C.

(Found: C, 44.68; H, 7.05; N, 8.62%. $C_6H_{11}O_4N$ requires C, 44.72; H, 6.88; N, 8.69%). $[\alpha]_{D20}$-16.6 ,c:, 0.27 in $H_2O$). m/z (DCI $NH_3$): 162 ($M+H^+$, 100%). $\delta_H$ ($D_2O$) 4.18 (1H, d, J 4.2 Hz), 3.84 (1H, dd, J 4.2 and 5.7 Hz), 3.42 (1H, dd, J 5.7 and 7.9 Hz), 3.17 (1H, dd, J 6.8 Hz), 1.15 (3H, d, J 6.5 Hz). $\delta_c$($D_2O$): 174.5 (s, C-1), 74.5, 74.1, 69.8 (3×d, C-2, C-3, C-4), 52.2 (d, C-5), 19.0 (q, C-6).

EXAMPLE 6

1,5-amino-1,5,6-trideoxy-D-mannitol hydrochloride [D-Deoxyrhamnojirimycin hydrochloride](5)

Borane:dimethylsulphide complex (10M, 0.5 ml) was added to a solution of the protected D-mannono-δ-lactam (13) 424 mg, 2.15 mmol) in dry tetrahydrofuran (10 ml). The reaction was stirred for 2 h under nitrogen. Methanol was then added until effervescence ceased. Solvents were removed under reduced pressure and methanol (2×10 ml) was distilled off the residue, which was dissolved in ethanol (5 ml). A few drops of concentrated aqueous hydrochloric acid were added and the reaction mixture was stored at −20° C. for 12 h. The crystals so obtained were filtered and washed with ethanol followed by ether to afford D-deoxyrhamnojirimycin hydrochloride 5as a white solid, (244 mg, m.p. 247°-248° C. (decomp). (Found: C, 39.40; H, 7.83; N, 7.38%. $C_6H_{14}O_3NCl$ requires C, 39.24; H, 7.68; N, 7.63%). [α]ze -35.7 (c, 0.60 in $H_2O$). m/z (DCI NH): 148 ($M+H$). $\delta_H$($D_2O$): 4.06 (1H, m), 3.47 (2H, m), 3.18 (1H, m), 3.02 (1H, m), 2.92 (1H, m), 1.23 (3H, d, J 6.5 Hz). $\delta_c$ ($D_2O$): 73.4, 72.3, 67.2 (3×d, C-2, C-3, C-4), 56.4 (d, C-5), 48.7 (t, C-1), 15.5 (q, C-6).

EXAMPLE 7

6-bromo-6-deoxy-2,3-O-isopropyliden-D-gulono-γ-lactone (16)

2,3-O-Isopropylidene-D-gulono-γ-lactone (15) (7.20 g, 33.0 mmol) was dissolved in tetrahydrofuran (100 ml) and cooled to 0° C. under nitrogen with stirring. Carbon tetrabromide (12.60 g, 38.0 mmol) and triphenyl phosphine (12.98 g, 49.5 mmol) were added and the reaction allowed to warm to room temperature over 2h and then stirred at room temperature for 10h when t.l.c. (ethyl acetate) revealed no starting material ($R_f$ 0.4) and one product ($R_1$ 0.9). The reaction was diluted with ether (100 ml), filtered and the solvent removed under reduced pressure. The residue was purified by flash column chromatography (ether/hexane 2:1) followed by recrystallisation from ether/hexane to yield 6-bromo-6-deoxy-2,3-O-isopropylidene-D-gulono-γ-lactone (16) as white needles (8.5 g, 85%). m.p. 86°-87° C. $[\alpha]_{D20}$−53.4 (c, 1.0 in $CHCl_3$), identical in all other respects to the enantiomer (10) above.

EXAMPLE 8

6-Deoxy-2,3-O-isopropylidene-D-gulono-γ-Iactone (17) The bromolactone (16) (8.59 g, 28.7 mmol) was dissolved in ethanol (50 ml). Triethylamine (5 ml) and palladium on carbon (10%, −50 mg) were added and the reaction was stirred under an atmosphere of hydrogen for 3 h when t.l.c. (ethyl acetate) showed no starting material ($R_f$9) and one product ($R_f$0.7). The reaction mixture was filtered through Celite and the solvent removed under reduced pressure. The residue was recrystallized from ethyl acetate to yield 6-deoxy-2,3-O-isopropylidene-D-gulono-γ-lactone (17) as a white solid (5.28 g, 91%). m.p. 142°-144° C., $[\alpha]_{D20}$ −62.5 (c, 1.5 in EtOH), identical in all other respects to the enantiomer (11) above.

EXAMPLE 9

5-Azido-5,6-dideoxy-2,3-O-isopropylidene-L-mannono-γ-lactone (18).

The deoxylactone (17) (4.97 g, 24.6 mmol) was dissolved in dichloromethane (50 ml) and cooled under dry nitrogen to −40° C. pyridine (2.98 ml, 36.9 mmol) and trifluoromethanesulphonic anhydride (27.1 ml, 45.6 mmol) Wer ⑧added and the reaction stirred for 1 h when t.l.c. (ethyl acetate/hexane 1:1) showed no starting material ($R_f$0.2) and one product ($R_f$0.8). The reaction mixture was washed with 50 ml aliquots of 2M hydrochloric acid, water and brine, dried (magnesium sulphate; and the solvents removed under reduced pressure. The crude triflate was dissolved in dimethylformamide (50 ml) and stirred at room temperature with sodium azide (4.80 g, 73.8 mmol) for 24 h when t.l.c. (ethyl acetate/hexane 1:2) revealed one product ($R_f$ 0.7). Solvents were removed under reduced pressure. The residue was dissolved in ethyl acetate (100 ml) and washed with brine (3×100 ml). The organic layer was dried (magnesium sulphate) and the solvents removed under reduced pressure. Purification by flash column chromatography (ethyl acetate/hexane 1:3) and recrystallisation from ether gave 5-azizo-5,6-dideoxy-2,3-O-isopropylidene-L-mannono-7-Iactone (18) as a white solid (4.43 g, 76%), m.p. 70°-72° C., [o]-4.64 (c, ( 0.8 in $CHCl_3$) identical in all other respects to the enantiomer (12) above.

EXAMPLE 10

6-Deoxy-1,2-O-isopropylidene-L-mannono-δ-lactam (19)

The azide (18) (3.20 g, 3.5 mmol) was dissolved in freshly distilled methanol (50 ml) and i0% palladium on carbon (−50 mg) was added. The reaction was stirred under an atmosphere of hydrogen for 5 h when t.l.c. (ethyl acetate/hexane 2) showed baseline material only and t.l.c. (10% methanol in ethyl acetate) showed one major product (Rf 0.6). The reaction mixture was filtered through Celite and the solvents removed under reduced pressure. The residue was purified by flash column chromatography (i? % ethanol in ethyl acetate) to yield 6-deoxy-I,2-O-isopropylidene-L-mannono-δ-lactam (19) as a hydroscopic foam, (2.57 g, 94%), $[\alpha]_{D20}$+17.4 (c, 0.34 in $CHCl_3$), identical in all other respects to the enantiomer (13) above.

EXAMPLE 11

6-Deoxy-L-mannono-δ-lactam [L-Rhamnonolactam](8)

The lactam (19) (250 mg, 1.24 mmol) was dissolved in trifluoroacetic acid (4 ml) and water (2 ml) was added. The reaction was left to stand for 2 h Wh®n t.l.c. (10% methanol in ethyl acetate) revealed no starting material ($R_f$ 0.6) and one product ($R_f$ 0.1). The solvents were removed under reduced pressure and toluene (2×5 ml) was distilled from the residue. The resulting solid was dissolved in the minimum quantity of hot ethanol and twice the volume of ethyl acetate was added to afford, after crystallization, L-rhamnonolactam (8) as a white crystalline solid (141 mg, 71%), $[\alpha]_{D20}+16.8$ (c, 0.31 in H$_2$O), identical in all other respects to the enantiomer (6) above.

EXAMPLE 12

1,5-Imino-1,5,6-trieoxy-L-mannitol hydrochloride [L-Deoxyrhamnojirimycin hydrochloride](7)

The protected L-mannono-δ-lactam (19) (237 mg, 1.2 mmol) was dissolved in dry tetrahydrofuran (5 ml) and borane:dimethylsulphide complex (10M, 0.5 ml) was added. The reaction was stirred for 12 h under nitrogen. Methanol was added until effervescence had ceased. Solvents were removed under reduced pressure and triturated with methanol (2×10 0 ml). The dissolved in ethanol (5 ml) and a few drops of concentrated aqueous hydrochloric acid were added. The reaction was stored at −20° C. for 12 h and the crystals so obtained were filtered and washed successively with ethanol and ether to yield L-deoxyrhamnojirimycin hydrochloride (7) as a white solid (177 mg. 84%). $[\alpha]_{D20}+37.5$ (c, 0.67 in H$_2$O), identical in all other respects to the enantiomer (5) above.

EXAMPLE 13

The D-Rhamnono-1,5-lactone (6) synthesized in the foregoing Examples was tested for its inhibitory activity against several enzymes in biological fluids, e.g. human liver extracts, and compared with similar enzyme assays for its L-epimer and deoxymannojirimycin (DMJ) and several other rhamnose and mannose derivative compounds. The enzymes included human liver glycosidases and naringinase. The latter enzyme is a readily available endo-L-rhamnosidase described by Romero et al., *Anal. Biochem.* 149, 566 (1985). The inhibition of human liver mannosidase by D-deoxyrhamnojirimycin (5) has been reported by Winchester et al., Biochem 269, 227 (1990). Using conventional methods of assay for enzyme inhibitory effects as described in said publications, the inhibition (%) at 1 mM concentration of these compounds of human liver glycosidases and α-rhamnosidase (naringinase) is set forth in the following Table 1:

TABLE 1

Effect of compounds on human liver glycosidases and α-rhamnosidase (naringinase) Inhibition (%) at 1 mM

| Compound | Human liver glycosidases | | | α-Rhamnosidase |
|---|---|---|---|---|
| | Lysosomal α-mannosidase | Lysosomal α-fucosidase | Others | |
| DMJ (1) | 58 ($K_i$, 7.5 × 10$^{-4}$ M) | 92 ($K_i$, 5 × 10$^{-6}$ M) | N-acetyl-β-D-hexosaminidase, 54 | N.D. |
| Mannono-1,5-lactam (2) | 94 ($I_{50}$, 5 × 10$^{-5}$ M) | 0 | cytosolic β-glucosidase, 98 ($I_{50}$, 5 × 10$^{-5}$ M) β-mannosidase, 99 ($I_{50}$, 1 × 10$^{-5}$ M) | 12 |
| 1,4-dideoxy-1,4-iminomannitol (3) | 89 ($K_i$, 13 × 10$^{-6}$ M) | 24 | β-galactosidase, 73 α-arabinosidase, 66 | — |
| D-Rhamnojirimycin (5) | 55 ($I_{50}$, 1 × 10$^{-3}$ M) | 90 ($K_i$, 7 × 10$^{-5}$ M) | — | 10 |
| D-Rhamno-1,5-lactam (6) | 86 ($I_{50}$, 1 × 10$^{-4}$ M) | 0 | cytosolic β-glucosidase, 67 ($I_{50}$, 7 × 10$^{-4}$ M) β-mannosidase, 40 | 3 |
| 1,4-dideoxy-1,4-imino-6-deoxy-mannitol (4) | 100 ($K_i$, 1.3 × 10$^{-6}$ M) | 21 | β-galactosidase, 65 α-arabinosidase, 91 | — |
| L-Rhamnojirimycin (7) | 19 | 0 | — | 0 |
| L-Rhamno-1,5-lactam (8) | 0 | 0 | — | 0 |

Various other examples will be apparent to the person killed in the art after reading the present disclosure without departing from the spirit and scope of the invention. It is intended that all such other examples be included within the scope of the appended claims.

What is claimed is:

1. D-Rhamnono-1,5-lactone.
2. A method for the synthesis of the D-rhamnono-1,5-lactone of claim 1 comprising the following steps:
   (a) 2,3-O-Isopropylidene-L-gulono-γ-lactone is converted to the 6-bromo derivative by reaction with carbon tetrabromide and triphenylphosphine;
   (b) The 6-Bromo der is subjected to catalytic hydrogenolysis to give the 6-deoxy derivative;
   (c) The unprotected hydroxyl function in the 6-deoxy derivative is esterified with triflic anhydride followed by displacement with azide salt to give the azide derivative;
   (d) The azide derivative is subjected to catalytic hydrogenation to cause reduction to the corresponding amine with spontaneous cyclization to the protected 6-deoxymannono-7-lactone;
   (e) The 6-deoxy-mannono-γ-lactone is deprotected by hydrolysis of the acetonide to give the desired D-rhamnono-1,5-lactone.
3. A method of inhibiting α- or β-mannosidase in a biological fluid containing α- or β-mannosidase comprising subjecting said biological fluid to an inhibitory effective amount of the D-rhamnono-1,5-lactone of claim 1.

* * * * *